United States Patent [19]

Hilal et al.

[11] Patent Number: 4,944,726
[45] Date of Patent: Jul. 31, 1990

[54] DEVICE FOR POWER INJECTION OF FLUIDS

[75] Inventors: Said S. Hilal, Laguna Niguel; Robert P. Cooper, Yorba Linda, both of Calif.

[73] Assignee: Applied Vascular Devices, Laguna Hills, Calif.

[21] Appl. No.: 266,200

[22] Filed: Nov. 3, 1988

[51] Int. Cl.$^5$ .............................................. A61M 5/145
[52] U.S. Cl. ...................................... 604/143; 604/70; 604/97; 222/389
[58] Field of Search ....................... 604/69, 70, 65, 97, 604/99, 131, 140, 141, 143; 417/401, 517; 222/389, 340

[56] References Cited

U.S. PATENT DOCUMENTS

| | | |
|---|---|---|
| 2,606,557 | 8/1952 | Stack . |
| 2,954,028 | 9/1960 | Smith . |
| 3,138,303 | 6/1964 | Hoveland ............................. 222/389 |
| 3,945,379 | 3/1976 | Pritz et al. ........................... 604/70 |
| 4,036,232 | 7/1977 | Genese ................................. 604/143 |
| 4,180,067 | 12/1979 | Derlien . |
| 4,332,254 | 6/1982 | Lundquist . |
| 4,439,185 | 3/1984 | Lundquist ............................ 604/97 |
| 4,525,156 | 6/1985 | Benusa et al. . |
| 4,529,397 | 6/1985 | Hennemuth et al. . |
| 4,666,430 | 5/1987 | Brown et al. ........................ 604/141 |

Primary Examiner—Stephen C. Pellegrino
Attorney, Agent, or Firm—Irell & Manella

[57] ABSTRACT

A hand-held and operated pneumatically powered device for injecting fluids, such as in medical applications, consisting of a housing that is sized and shaped to be hand held, and connected power and infusion assemblies contained within the housing. The power assembly includes a sealed vessel containing pressurized gas, a lever-needle vessel-puncturing mechanism, a gas flow path leading from the needle to the infusion assembly, and pressure regulator and pressure relief mechanism (which may include a pneumatic flow control orifice) interposed in the flow path. The infusion assembly includes a two-way valve for exhausting the gas or directing it into a power chamber for receiving the gas connected in tandem with an infusion chamber that holds the infusate, a two-headed piston contained within and spanning the two chambers with one of its heads in contact with the pressurized gas and the other in contact with the infusate, and a throttle mechanism at the outlet of the infusion chamber for regulating the pressurized flow of infusate into and out of the infusion chamber by means of a two-way valve. A pressure gauge may be provided for measuring the pressure of the infusate.

In one embodiment, two power infusion devices are coupled together with a common pressurized gas source and are also coupled together at their outlets for providing two different infusates to the proximal and distal ends of a catheter. A ball valve is utilized to purge the infusates of entrapped gas.

28 Claims, 6 Drawing Sheets

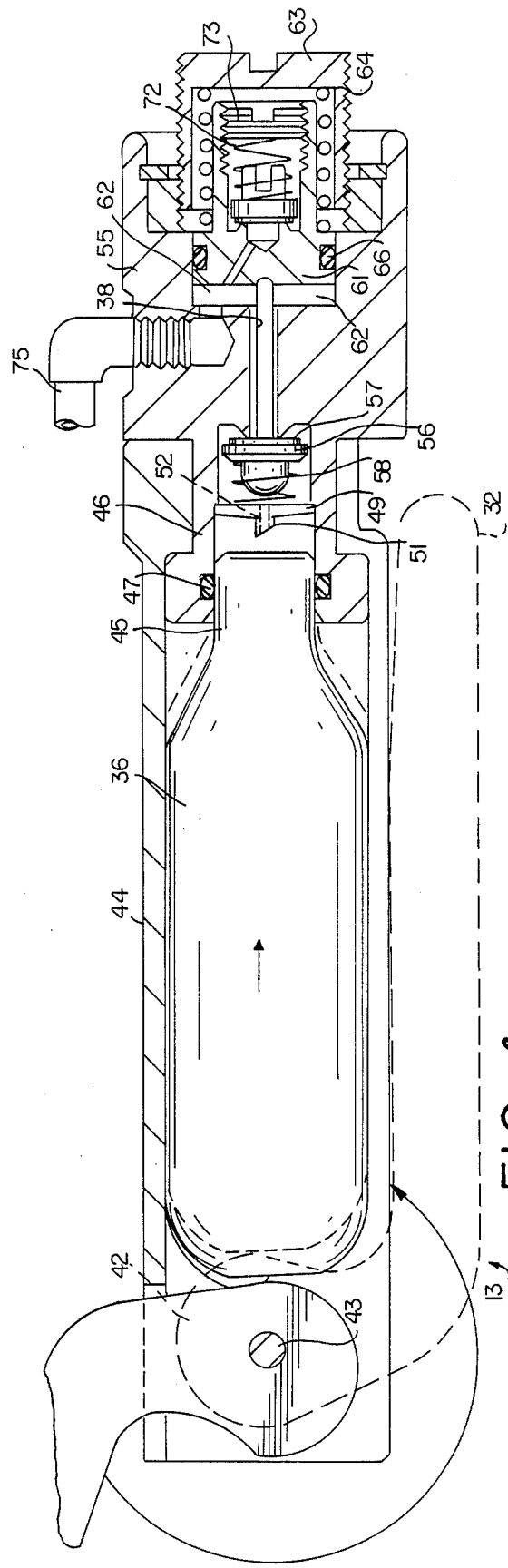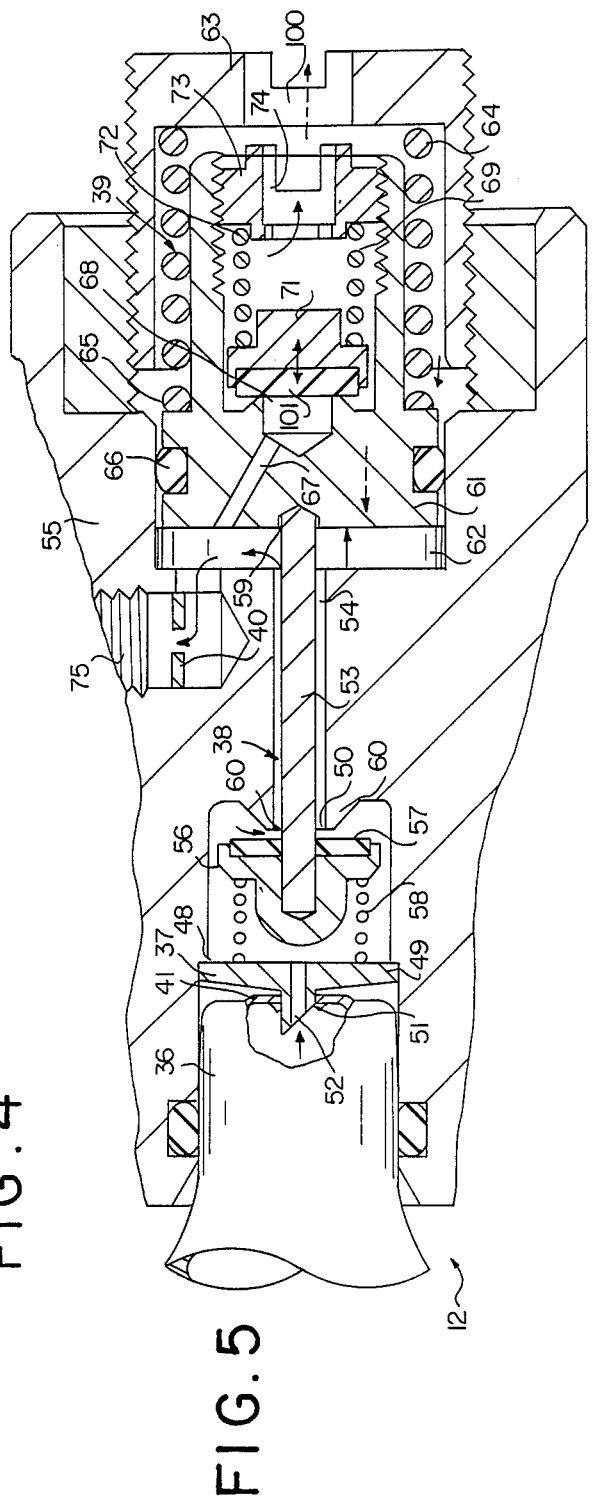

DEVICE FOR POWER INJECTION OF FLUIDS

DESCRIPTION

1. Technical Field

The invention relates to the power injection of fluids in medical or commercial applications. In medical applications the invention is useful in injecting dye and medical solutions into patients and catheters or inflation medium into dilatation balloons.

2. Background Art

Injection of fluids during diagnostic and therapeutic procedures is conducted millions of times every year. The purpose of the practice is to propel saline, medication or radiopaque dye solutions into cavities or blood vessels of patients.

Generally, injection of dyes is done frequently and elaborately during diagnostic procedures, where mapping of the anatomy is required for further evaluation. But dye injection is also needed during therapeutic procedures, such as angioplasty, in order to enable the physician to evaluate catheter location, condition of the lesion, nature of the stenosis, progress of the procedure and effectiveness of the dilatation.

Infusion of various solutions requires the propulsion of said solutions through often long, narrow and tortuous paths. The dye, even when diluted to fifty or seventy-five percent concentrations, remains viscous and relatively hard to propel within the small lumens of catheters. Increasingly, smaller lumen catheters are being used to accommodate new, less invasive procedures. Medical personnel are now faced with inadequate infusion capabilities due to the lack of appropriate means of infusion.

Currently, infusion during diagnostic angiographic procedures is conducted in catheterization laboratories equipped with large injection equipment such as the Medrad Injector. The equipment is expensive, large and not suited for use in the special interventional, i.e. therapeutic, procedures. Also, much of the need in such procedures is for the small bolus injections where the physician desires to maintain a "feel" for the injection process and corresponding patient response. Large infusion devices do not accommodate such a requirement.

As such, there is a distinct and important need for a means for injecting solutions and dyes in relatively small quantities while the physician is maintaining a "feel" for the process, with equipment that is compact and easy to use without the need for brute strength to effect the injection.

With the exception of major diagnostic procedures, most infusions are done manually with a standard syringe, possibly equipped with a handle or a grip. Obviously, generating sufficient pressure for adequate infusion or inflation is dependent on the strength of the operator. Past attempts at supplying the clinicians with pneumatically powered infusion devices have fallen short due to legitimate technical needs such as loss of control, lag time, increased cost and safety issues, to name some.

A subsegment of the above need is related to the infusion and aspiration of solutions to inflate or deflate dilatation balloons. Products that address such needs are known as inflation devices.

In the inflation device area, a gamut of devices with some mechanical assistance emerged. Such devices typically include a housing, a syringe carried by the housing and comprising a rigid plunger connected to a piston and extending out of the housing, and a ratchet mechanism to assist in applying load to the plunger. Such devices are described in numerous patents and are well known. Examples are U.S. Pat. Nos. 4,439,185 and 4,332,254. Usually, such devices incorporate means to engage and disengage the plunger from the ratchet mechanism to permit the user to apply unassisted hand power to achieve all or part of the desired pressures. This feature often introduces the added disadvantages of a mechanical button or lever that must move while under load to cause the engaging or disengaging of the ratchet mechanism. Such a requirement is sometimes difficult and always cumbersome.

Such devices, obviously, possess shortcomings as inflation apparatus but, more importantly, all are unsuitable as infusion devices for the reasons discussed above. The combination of characteristics of prior devices makes these devices unsuitable for either rapid or easy injection of dyes. Thus the need for compact, controllable, or hand-held injection and inflation devices that provide injection power while maintaining the user's ability to "feel" the process remains largely unmet.

In general, it is the object of this invention to provide a compact, economic and efficient means of infusing medical solutions into patients, catheters or dilatation balloons while maintaining the user's ability to estimate or evaluate the impact of said infusion or inflation on the patient in order to adjust and optimize the course of the ongoing therapy.

Another objective of the invention is to provide an ergonomic infusion, inflation and deflation device which can be operated by the single hand of an operator.

Another objective of the invention is to provide a means of infusion and inflation without the requirement of considerable hand strength from the operator.

Another objective of the invention is to provide a powered infusion/inflation device that is easy to fill with the infusion/inflation medium.

Another objective of the invention is to keep the pneumatic power system isolated from the fluid to be infused, said isolation to be accomplished without the introduction of mechanical linkage that may fail or break.

SUMMARY OF THE INVENTION

The invention is a hand-held and operated pneumatically powered infusion/inflation device comprising in combination (a) a housing adapted to be gripped and held by a human hand and containing (b) a pressure vessel containing a gas under pressure (c) valve means connected to the vessel for venting the gas or directing it to (d) a power-infusion chamber assembly comprising (i) a power chamber having an inlet for receiving said gas and being connected in tandem to (ii) an infusion chamber for holding an infusate having an outlet through which the infusate is ejected under the pressure exerted by said gas (iii) a two-headed piston contained within and spanning the power and infusate chambers with one head positioned in the drive chamber and receiving pressure from the gas and the other head positioned in the infusion chamber and placing pressure on the infusate (iv) a pressure gauge for reading the pressure within the infusion chamber (e) a second valve means connected to said outlet for controlling the pressurized flow of infusate from the infusion chamber; and (f) a conduit connected to said valve means for carrying the infusate from the valve to the infusion/inflation site.

Two units as described above may be coupled together with a common pressurized gas source, and connected at their outlets with four valves for allowing the operator of the device to provide a first infusate and a second infusate to each of a first and second infusion location, such as the proximal and distal ends of a catheter. Ball check valves or similar venting devices are provided to purge the infusate of gas, and check valves are provided to prevent backing up of the fluids into the infusate reservoirs or into the infuser devices from the catheter.

BRIEF DESCRIPTION OF THE DRAWINGS

FIG. 4 is an enlarged, sectional view of the power system assembly of the device of FIG. 1, with the power system disengaged.

FIG. 5 is an enlarged, sectional view of a portion of the assembly of FIG. 4 showing the operation of the pressure regulator and pressure relief mechanism thereof.

DESCRIPTION OF THE PREFERRED EMBODIMENTS

Figure 1:
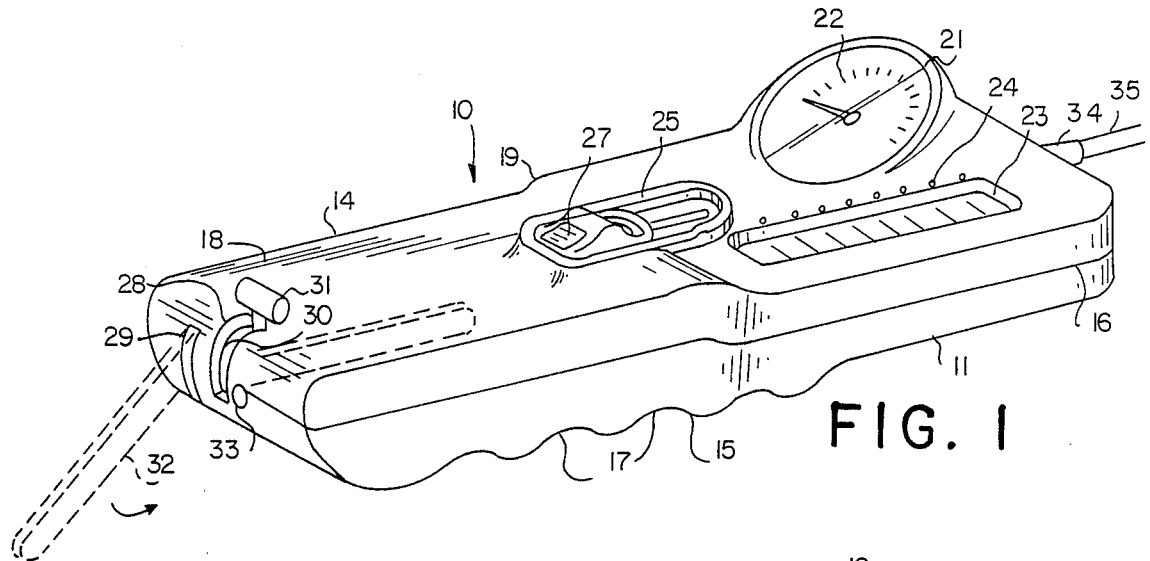
FIG. 1 is a orthogonal partly schematic view of an embodiment of the invention device.
Figure 2:
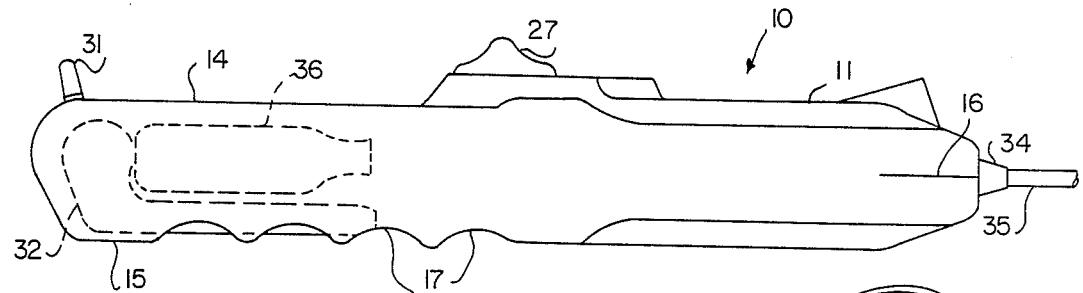
FIG. 2 is a side view of the device of FIG. 1.
Figure 3:
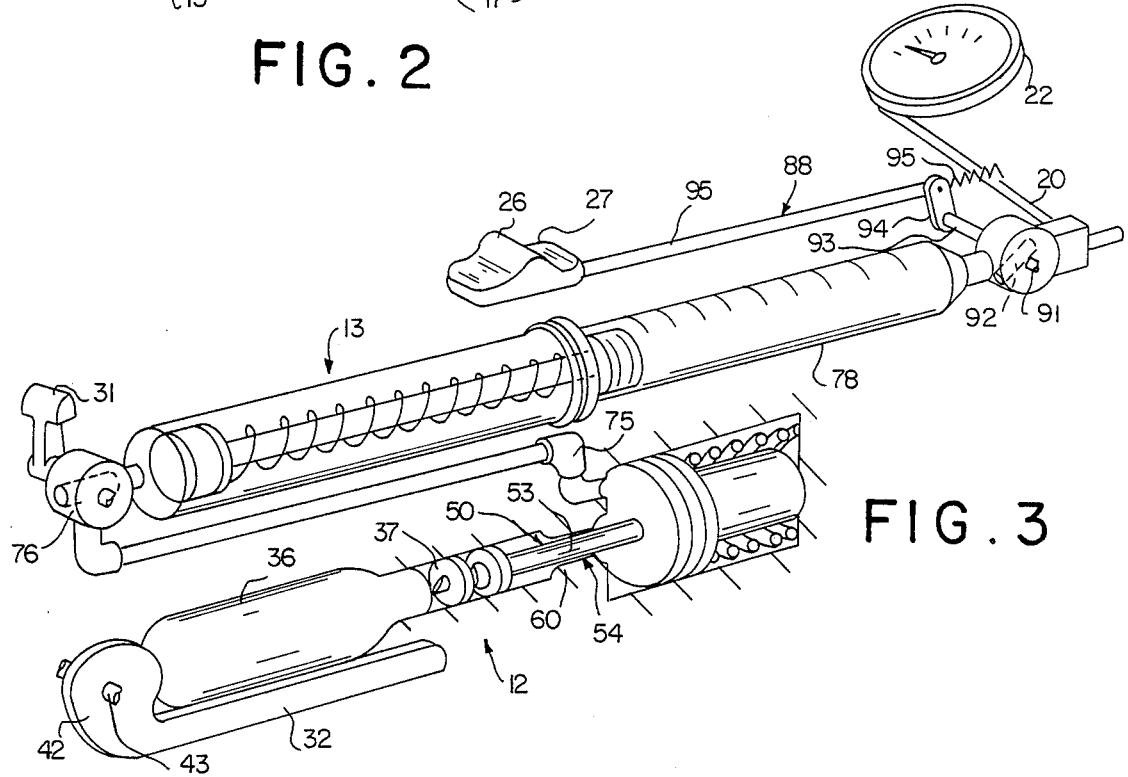
FIG. 3 is an orthogonal view of the principal working elements of the device of FIG. 1.

FIGS. 1-3 depict a power infusion device, generally designated 10, that is adapted to be held in a human hand and operated manually. FIGS. 1 and 2 show the general profile and appearance of housing 11 of the device and FIG. 3 illustrates the two assemblies that are contained within the housing and that constitute the working elements of the device: a pneumatic power system assembly 12 and a power infusion chamber assembly 13.

Housing 11 is generally rectangular in shape and includes an upper half 14 and a lower half 15 that are sealed or otherwise joined at their periphery 16. The housing is sized and shaped to be gripped comfortably by a human hand. To facilitate such handling, the lower half of the housing has four transverse finger holds 17 in its bottom wall, and the rear end 18 of the housing is narrowed at 19. The upper half of the housing has five openings in it for receiving various device control and monitoring mechanisms. Specifically, the front end of the top half 14 of the housing 11 has an opening 21 in which is seated a pressure gauge 22 and an opening 23 through which the contents of infusion cylinder or chamber 78 (see FIGS. 3 and 6) of assembly 13 may be viewed. The gauge 22, its coupling conduit 20 (shown in FIG. 3), and the cylinder 78 may be substantially coplanar to minimize the possibility of air being trapped, and to facilitate the purging of air from the system, as described below.

Figure 9:
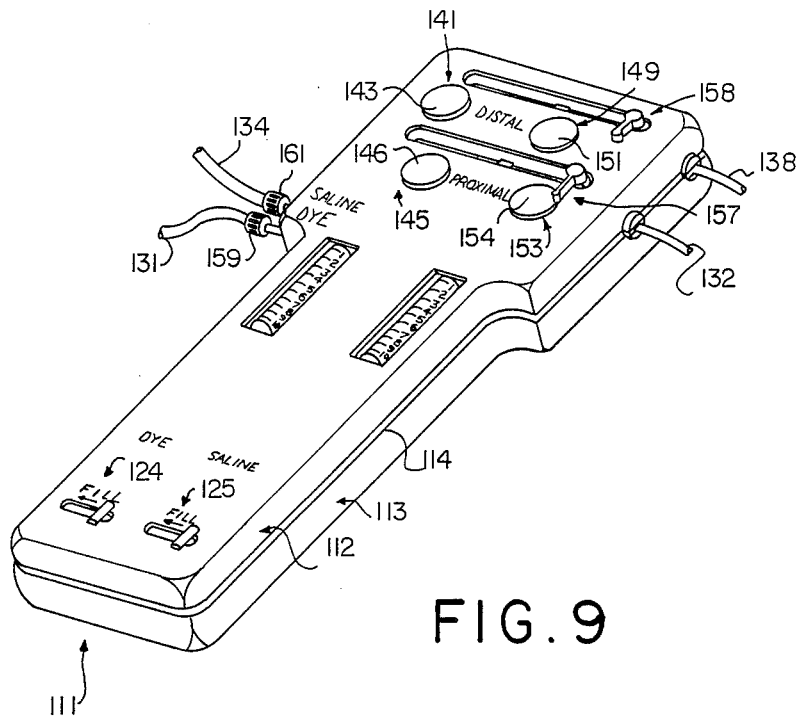
FIG. 9 is a perspective view of a dual-chamber assembly.

Opening 23 is flanked by a series of markings 24 by which the volume of contents of the cylinder 78 may be read. Alternatively, or in addition, the cylinder 78 itself may be graduated, as shown in FIG. 9. A third opening 25 spans the middle of the upper half 14, is longitudinally elongated and raised, and receives a valve actuator 26 of an injection medium throttle mechanism 88 (FIG. 3). Valve actuator 26 has a generally sinusoidal shape and has serrated thumb holds 27 on either side of it to facilitate switching the throttle mechanism on and off with the thumb.

Fourth and fifth openings in the upper half 14, numbered 28 and 29, respectively, extend down into the bottom half 15 of the housing 11 and receive, respectively, a valve handle 31 for controlling a valve 76 (FIG. 3) in a connector line or tube 75 between the power assembly 12 and infusion chamber assembly 13, and a lever handle 32 for activating the pneumatic power assembly 12. The rear end of the housing also has a vent hole 33 for use in venting the power or drive chamber of the infusion chamber assembly. The front end of the housing has a boss 34 that defines an opening that receives a conduit 35 for carrying the infusion medium from the device to the infusion site. Alternative means for venting the housing 11 may be provided, such as by ensuring that the housing is not gas-tight, such that the pressurized gas, once spent, may escape through any of several venting paths, which may include the opening 23 or opening 30 adjacent the valve handle 31.

FIGS. 2-5 illustrate the pneumatic power assembly 12 and its operation. The assembly 12 is housed within housing 11. Its basic components are lever 32, a pressure vessel 36 containing a gas (such as $CO_2$) under pressure, a vessel puncturing member 37, a pressure regulator mechanism, generally designated 38, and a relief valve mechanism, generally designated 39. FIGS. 3 and 4 show the power assembly before it is activated. Activation occurs when the sealed end 41 of the vessel 36 is punctured, thereby allowing gas to escape from the vessel into the system.

The vessel 36 is punctured through the interaction of lever 32, vessel 36 and the puncturing member 37. Once the lever 32 is rotated into the position shown in FIG. 21, it remains there until the pressure vessel 36 is replaced.

Cam head 42 of the lever 22 is mounted on a shaft 43 that extends across opening 29. As the lever is rotated from its open position (FIG. 1 in phantom) to its tucked position (FIGS. 2, 3 and 4), the cam works against the rear end of the vessel. The body of the vessel is slidably housed within a sleeve 44 with its neck 45 slidably housed within the rear end of an inner sleeve 46. The neck is sealed within sleeve 45 by an O-ring 47. Rotation of the cam lever thus biases the vessel forwardly in the sleeves and brings the puncturing member 37, which is sealingly seated within sleeve 46 against a shoulder 48, into contact with the sealed end of the vessel (forward motion depicted in phantom in FIG. 4). Member 37 comprises a disc-shaped body 49 having a rearwardly extending needle element 51 with a central bore 52 extending through the needle and body. Further forward movement of the vessel causes the needle 51 to puncture the sealed end of the vessel 36, thus permitting gas to flow therefrom into the forward end of the lumen of sleeve 46 via bore 52 (see FIG. 5). Once the vessel 36 is pierced, the forward end thereof remains in contact with the O-ring 47 until the vessel is affirmatively removed, thus sealing the pressurized gas from the atmosphere and preventing it from escaping.

The escaping gas is permitted to flow from the forward end of the lumen of sleeve 46 by the action of regulator mechanism 38. That mechanism includes a cylindrical rod 53 that is loosely received through a counterbore 54 in the forward end 55 of sleeve 46 having a cap or head 56 that resides in the front end of the lumen of sleeve 46. The forward surface of head 56 carries a seal 57 that is adapted to seat against and close the rear opening 50 of counterbore 54 at a seat 60. A coil spring 58 resides between the front face of body 49 and the rear surface of head 56 for urging the regulator mechanism forwardly. The forward end of rod 53 is seated in a notch 59 in the rear surface of main body 61 of the relief valve mechanism 39.

As shown in FIGS. 4 and 5, body 61 is slidingly received in a cavity defined by an opening 62 in the forward end 55 of sleeve 46 and an end cap 63 that is threadedly received into the mouth of opening 62. A large coil spring 64 is seated between the underside of a shoulder 65 on the exterior of body 61. Spring 64 biases the body 61 and the regulator mechanism 38 rearwardly such that seal 57 is normally spaced from the rear opening of bore 54, thus providing a passageway from the front end of the lumen of sleeve 46 through bore 54 into opening 62.

The outer longitudinal edge of body 61 is pneumatically sealed against the inner side wall of opening 62 by an O-ring 66. It will be appreciated that when the pressure within opening 62 rearwardly of O-ring 66 is sufficient to force body 61 forwardly, spring 58 is permitted to bias head 56 forwardly so that seal 57 covers the opening to bore 54 and closes off the source of pressurized gas until said pressure is relieved in opening 62 to a point where spring 64 forces the seal 57 away from the opening to permit renewed flow of pressurized gas into the opening.

Body 61 contains a safety release mechanism to relieve excess pressure, including a diagonal bore 67 extending from the forward end of opening 62 into a bore 68 in the forward end of a larger bore 69 in the forward end of body 61. The mouth of bore 68 is normally sealed by a valve 71 having a seal 101 and held in place by a spring 72 seated between the valve 71 and the inner side of a plug 73 that is threadedly received in the forward end of bore 69. Plug 73 has a central opening 74 through it that opens to the atmosphere via port 100. When the pressure of gas within the portion of opening 62 forward of the O-ring is great enough to overcome the pressure exerted on valve 71 by spring 72, it forces the valve out of contact from the mouth of bore 68 thus permitting the pressure to be vented via bores 67, 68 and 69, opening 74, and port 100, until the gas pressure drops to a level which is predetermined by the spring constant of the spring 72. It will be appreciated that under normal operating conditions the pressurized gas flows from opening 62 into a connector tube 75 which connects the pneumatic pressure assembly 12 to the infusion chamber assembly 13. A flow control orifice 40 may be formed adjacent or in the tube 75 (as shown in FIG. 5) for pneumatic flow control of the pressurized gas, and in particular to restrict the flow of the pressurized gas to prevent it from overdriving the power cylinder 77.

Figure 6:
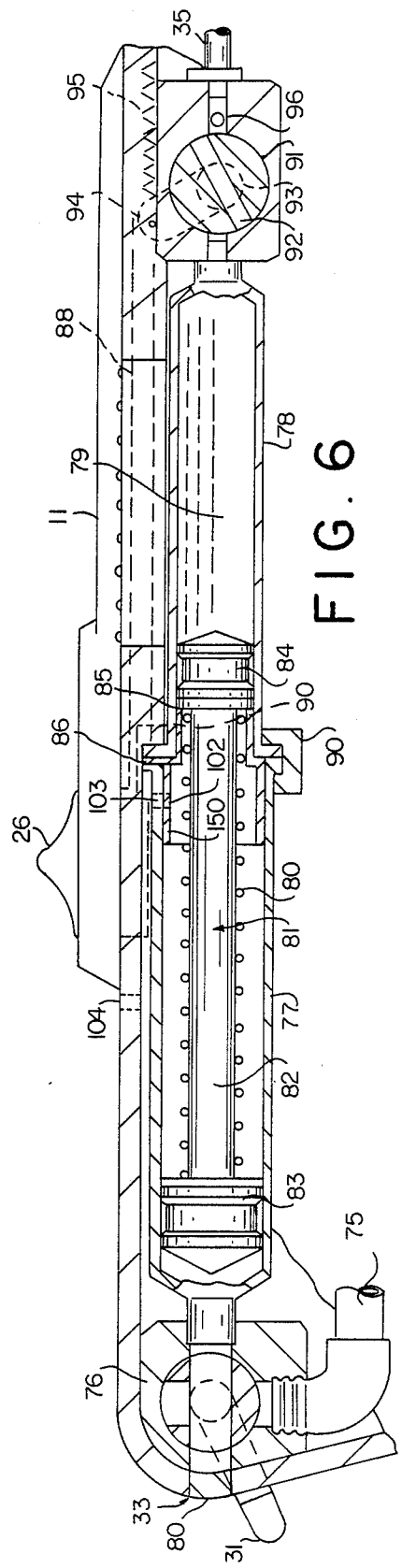
FIG. 6 is an enlarged, sectional view of the infusion chamber assembly of the device of FIG. 1 showing the assembly prior to infusion.
Figure 7:
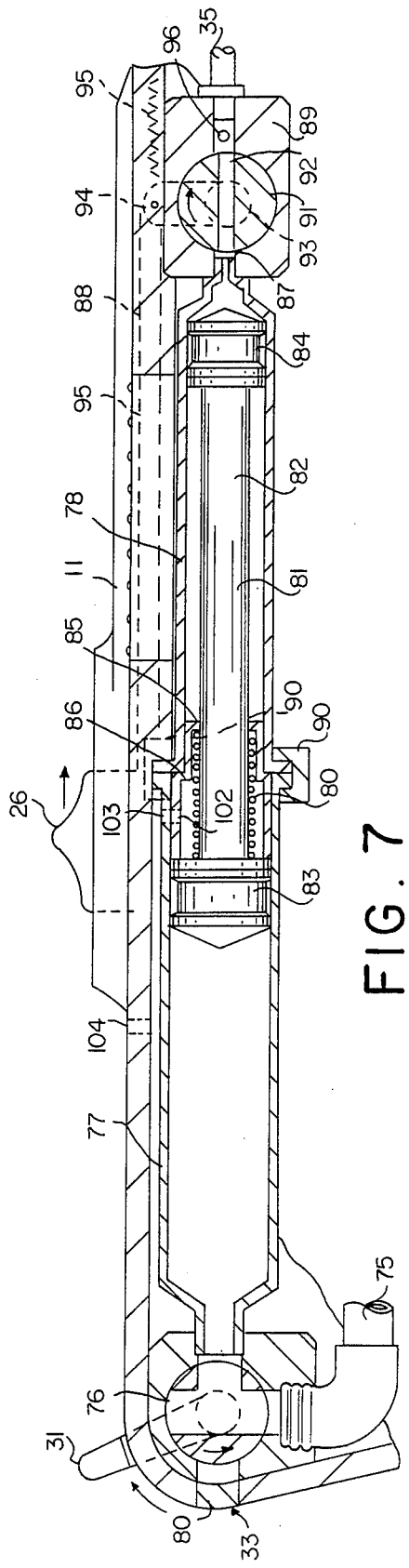
FIG. 7 is an enlarged, sectional view of the infusion chamber assembly of the device of FIG. 1 showing the assembly after infusion.

The power infusion chamber assembly 13 and its mode of operation are shown in FIGS. 3, 6 and 7. It is also carried within the housing 11. There is a two-way valve 76 at the power infusion chamber assembly end of connector tube 75 that permits the tube to connect to the power chamber of the power infusion chamber assembly or be shut while the gas in the chamber is vented to atmosphere. A pneumatic silencer 80 may be provided at the vent hole 33, as shown in FIGS. 6 and 7.

FIG. 6 shows the venting position, while FIG. 7 shows the power chamber connecting position, of valve 76. The assembly 13 includes a rear power cylinder 77 which receives the pressurized gas, with the infusion cylinder 78 having a smaller diameter than the cylinder 77. The cylinder 78 is connected in tandem to the cylinder 77 and contains the infusion medium 79 to be discharged. Cylinder 78 is made of a clear material so that its contents may be viewed through opening 23.

The cylinders 77 and 78 may be held in a fixed relative position by means of an assembly retaining clip 90. Together the cylinders 77 and 78 define a continuous chamber in which is contained a two-headed piston, generally designated 81. The piston 81 includes a connecting rod 82, a large head 83 that is reciprocatingly received in cylinder 77 and a smaller head 84 that is similarly received in cylinder 78. The heads 83 and 84 act as seals for the piston 81. There are stops 85 and 86 at the respective inner ends of the cylinders to limit the extent to which the piston may move reciprocally with the cylinders. A spring 80 sits between the forward side of head 83 and the rear side of stop 85 so that the piston is normally biased rearwardly by the spring action. The channel of the two-way valve 76 opens into the rear end of cylinder 77.

The front end of cylinder 78 opens into the channel 87 of an infusion throttle mechanism, generally designated 88. The throttle mechanism is used to control the flow of infusion medium from cylinder 78. It includes a valve housing 89 through which channel 87 passes longitudinally, and a rotatable valve body 91 also having a channel 92 through it. The valve body is connected to a shaft 93 which in turn is connected to a connecting arm 94. A spring 95 is seated against the top of the connecting arm so that it is normally biased rearwardly. The top of the connecting arm 94 is in turn connected to an elongated rod that terminates at its rearward end with valve actuator 26. The normal (closed) position of the valve 91 is shown in FIG. 6. Due to the action of spring 95 the connecting arm is biased rearwardly, which causes valve body 91 to be rotated such that its channel 92 does not register with the channel 87 through the valve housing. The valve is moved to its open position (FIG. 6) by moving valve actuator 26 forward. This action causes the connecting arm to move forward and rotate the valve body so that its channel 91 is partly or wholly in registry with channel 87, thus providing a flow path from (or to) cylinder 78. The conduit 35 is connected to front end of channel 87 to extend that flow path. Pressure gauge 22 connects into channel 87 forwardly of the valve body at junction 96.

In disposable versions of the device the pressure vessel and infusate cylinders are permanently in place. It will be appreciated, however, that the device may be designed and constructed so that either or both of these units are removable and replaceable so as to permit the device to be reusable.

The device is operated as follows. The infusion medium 79 may be preloaded into cylinder 78 or loaded as follows. With valve 76 in its power (non-exhaust) position (FIG. 7), valve 91 closed (FIG. 6) and the conduit 35 open to atmosphere, the pneumatic power assembly is activated by rotating lever 32 as described above, thus connecting the source of pressurized gas to cylinder 77. This will cause the pressurized gas to enter chamber 77 and move the piston 81 forward. Valve 91 is then opened by pushing the valve actuator 26 forward, thus permitting any original air in chamber 79 to be purged (FIG. 7). Valve 91 is then closed and conduit 35 is connected to the source of infusion medium, not shown. Valve 76 is then rotated to its vent position (FIG. 6) which will cause the spring 80 to drive piston 81 rearwardly and create a vacuum in cylinder 78. When valve 91 is opened, the medium will be drawn into cylinder 78. Valve 91 is then closed by releasing the valve actuator 26 and valve 76 is moved to its nonexhaust (FIG. 7) position, and the conduit is disconnected from the source of medium. The device is thus loaded with medium.

To eject the medium for infusion or inflation purposes, the conduit 35 is connected to the infusion/inflation site, either directly or indirectly through additional conduits, and the valve actuator is pushed forwardly to open valve 91, thus permitting the medium to flow under the pressure exerted on it by the pressurized gas and piston 81 through the valve channel and conduit 35 to the infusion/inflation site. The rate of flow is controlled by the distance the valve actuator is moved. The infusion pressure may be monitored via gauge 22 and the volume of infused medium ejected via opening 23.

It will be appreciated that, if the operator of the device should release the valve actuator 26, such as in the case of a slip of the finger, the valve 91 automatically returns to its closed configuration as shown in FIG. 6, due to the spring 95 forcing the arm 94 back, i.e. to the left as seen in FIG. 6. This removes the pressure from the infusion medium 79 in the conduit 35, and thus eliminates any pressure provided to the patient.

Another safety feature of the present invention relates to ports 102, 103 and 104 provided in wall 105, cylinder 77, and wall 106, respectively, as shown in FIGS. 6 and 7, and to the fact that the invention utilizes a double-headed piston 81 (rather than, for instance, a single-headed piston). This combination of features prevents any of the pressurized gas from mixing with the infusate which is provided to the patient. Ports 102, 103 and 104 are provided to bleed off to atmosphere any pressurized gas which might possibly leak past the head 83, such that any such leaking gas will preferentially flow out of these ports rather than flowing into the infusate 79. In addition, the head 84 acts as a further blockage to any such leaking gas, so that it will not reach the infusate.

Figure 8:
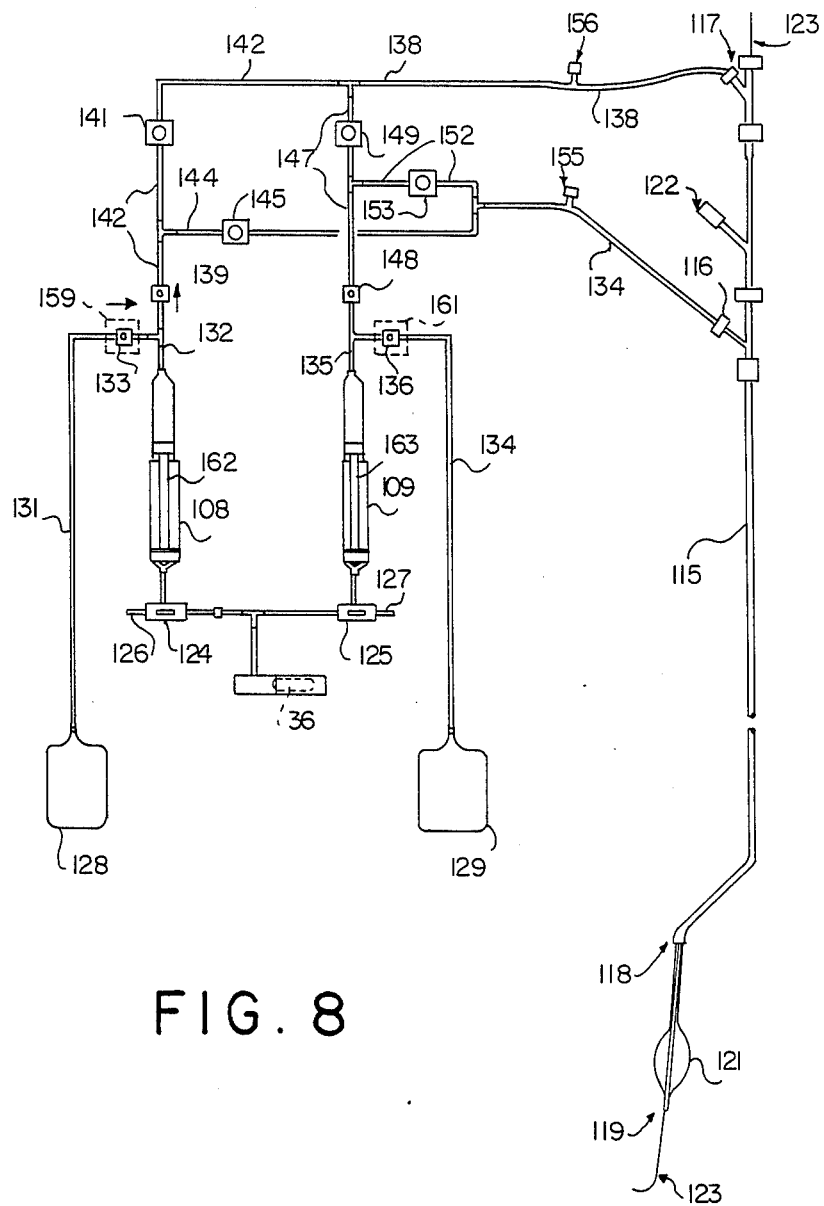
FIG. 8 is a schematic diagram of a catheter system utilizing the present invention.

FIGS. 8 and 9 show an embodiment of the invention wherein two power infusion devices 108 and 109 are utilized, and are both contained within a housing 111 having an upper half 112 and a lower half 113 fixed together in a sealed fashion at a junction 114.

FIG. 8 is a schematic diagram of the invention in use with a conventional catheter 115 (not drawn to scale) having an input 116 and an input 117, which are connected, respectively, to a proximal output 118 and a distal output 119. The catheter 115 may include other features, such as an inflatable balloon 121 coupled to an inflation input 122, and a guide wire 123.

The structure of the devices 108 and 109 is the same as that described above relative to FIGS. 1–7. In this embodiment, however, a single pressure vessel 36 is utilized, rather than utilizing one pressure vessel for each power infusion device 108 and 109. The vessel 36 in the embodiment of FIGS. 8 and 9 is activated by a puncturing mechanism in the same manner as the vessel 36 in the embodiment of FIGS. 1–7, though the structures (including the lever handle 32 and the puncturing mechanism 37) are not separately shown in FIGS. 8 and 9.

Two two-way valves 124 and 125 are provided, and are of the same design as the valve 76. Each valve 124 and 125 has a vent (126 and 127, respectively) such that when valves 124 and 125 are in the position shown for valve 76 in FIG. 6, venting to atmosphere is accomplished.

Reservoirs 128 and 129 are provided, and may include dye and saline, respectively, or other infusion media. A tube 131 is connected to conduit 132 (corresponding to conduit 35 in FIGS. 6 and 7), via a one-way check valve 133 which allows infusate to flow only to the right as shown in FIG. 8. A tube 134 is likewise connected to the reservoir 129 via a conduit 135, which corresponds to conduit 35. A check valve 136 is provided, and allows fluid to flow only to the left as shown in FIG. 8.

The device 108 is coupled to both the proximal input 116 via a proximal input tube 137 and to the distal input tube 117 via a distal input tube 138. A one-way check valve 139 is coupled to the output of the conduit 132, with fluid flowing only in the direction of the arrow shown in FIG. 8. A valve 141 is provided along tube 142, which connects conduit 132 to distal input tube 138. The valve 141 is normally closed, and when it is opened (such as by pressing button 143 shown in FIG. 9), the tube 142 is thereby open to allow fluid to flow therethrough and into the distal input 117. When the button 143 is released, a spring bias or other biasing mechanism automatically closes the valve 141.

The conduit 132 is also coupled to the proximal input 116 via a tube 144 in which a valve 145 is situated, and is activated by a button 146. The valve 145 is identical to the valve 141. Thus, if the reservoir 128 contains dye, the tubes 142 and 144 and valving structure described allow for the provision of dye at both the proximal input 116 and the distal input 117.

Similarly, saline from reservoir 129 is provided to the proximal and distal inputs 116 and 117. The saline is provided to distal input 117 via a tube 147 having a valve 149 which is activated by a button 151, and is identical to the valve 141. Saline is provided to the proximal input 116 via a tube 152 having a valve 153 identical to the valve 141 and actuable by a button 154. A check valve 148, identical to the check valve 139, is coupled to the output of the conduit 135, to ensure that fluid flows only in the direction of the vertical arrow adjacent the valve 148 as shown in FIG. 8.

Bleeder valves 155 and 156 are provided in the proximal and distal input tubes 137 and 138, respectively, and are utilized in a manner to be described below. The bleeder valves 155 and 156 are preferably at a physically higher point than the other parts of the system, except for the reservoirs 128 and 129. The bleeder valves 155 and 156 are actuated by means of spring-biased, normally closed valve switches 157 and 158, respectively.

The valves 155 and 156 may alternatively be automatic air vent valves, such as ball valves. In this case, the ball valves may be automatic, but with manual override.

The system of FIG. 8 is operated in much the same manner as the embodiment described relative to FIGS. 1–7 above, with additional features as in the following discussion. Reservoirs 128 and 129 are coupled to the conduits 132 and 135, respectively, while tubes 137 and 138 are not yet coupled to the inputs 116 and 117. Typically, reservoirs 128 and 129 will be placed at a high position (such as on an IV rack) and air will bleed from the tubes 131 and 134 before connecting them to the conduits 132 and 135. The connections to the conduits 132 and 135 may be accomplished by means of standard connectors 159 and 161, respectively, as shown in FIG. 9. In one embodiment, the check valves 133 and 136 are contained within the connectors 159 and 161, as indicated in FIG. 8.

The connection of the reservoirs 128 and 129 is preferably done with the pistons 162 and 163 (which are analogous to piston 81 shown in FIGS. 6 and 7) in their forward position, just as the piston 81 is in its forward position in FIG. 7. Thus, valves 124 and 125 are operated to drive the pistons 162 and 163 forward, thus exhausting any air which may be present within the devices 108 and 109. Then the reservoirs 128 and 129 are coupled as described above.

Valves 124 and 125 are then operated to draw dye into the device 108 and saline into the device 109, respectively, as described above relative to the single-injector embodiment of FIGS. 1–7. Note that the check valves 139 and 148 prevent any air from being drawn through tubes 142 and 147 into the devices 108 and 109.

The device 108 is then operated to force dye into the tube 142, and the valves 141 and 145 are opened, to allow dye to flow to the bleeder valves 156 and 155, respectively. Similarly, saline is provided through the valves 149 and 153 to the tubes 138 and 137, respectively. Typically, fluid would be allowed to flow out of the tubes 138 and 137, in order to ensure that no air is trapped in the system and then the tubes 138 and 137 are coupled to the inputs 117 and 116, respectively. Additional infusion medium may be drawn into the devices 108 and 109, if desired, to make up for volume lost through the bleeding procedure, and bleeding may again be carried out.

The system is now ready for use with a patient. The valves 124 and 125 are operated to pressurize the power infusion assembly (thereby loading the springs to the position shown in FIG. 7) to provide the desired amount of dye and saline into the devices 108 and 109. Either dye or saline or both may be provided to the proximal and the distal outputs 118 and 119 as shown in FIG. 8. For instance, to provide saline to the proximal end 118, the operator presses button 154, which activates valve 153 and allows saline to flow into the proximal input 116. Likewise, dye may be provided to the proximal input 116 by depressing the button 146 and either dye or saline may be provided to the distal input 117 by depressing the buttons 143 and 151, respectively. Before dye or saline is actually provided to the patient, the operator opens the bleeder valves 155 and 156, to allow some fluid to flow therethrough, thus bleeding any air from the system in order to prevent injury to the patient.

It will be appreciated that additional devices such as 108 and 109 may be provided and coupled to additional reservoirs such as 128 and 129, such that a multi-unit infusion device results and operates on the same principles as the dual-reservoir device as described relative to FIGS. 8 and 9.

Figure 10:
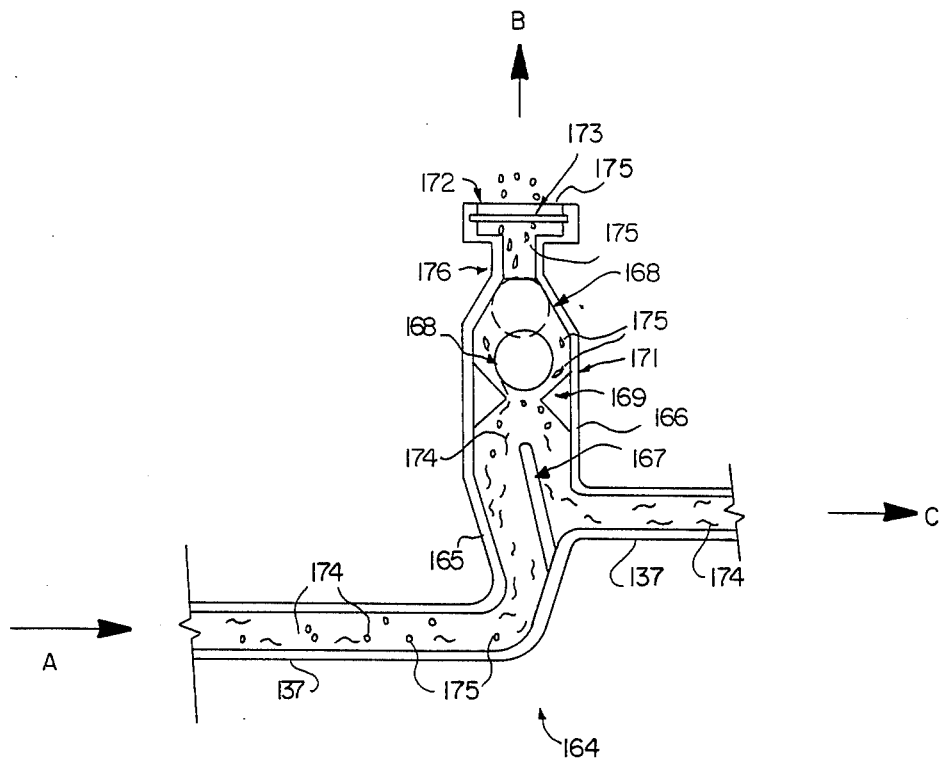
FIG. 10 is a cross-sectional view of a ball valve for use with the present invention.

FIG. 10 shows a ball valve 164 which may be used in place of either or both of the bleeder valves 155 and 156. The valve 164 has an inlet end 165 and an outlet end 166, which are coupled into the proximal input tube 137. A baffle 167 is mounted between the inlet 165 and the outlet 166, and is substantially vertically disposed to provide a vertical barrier. A ball 168 is shown in its "up" and "down" positions, and when it is in the down position it rests on an annular ball stop 169. A vertical valve body 171 carries the ball stop 169, and includes a port 172 carrying a sterile air barrier 173.

As fluid 174 flows into the inlet 165, as indicated by arrow A in FIG. 10, it may contain bubbles 175 of air or some other gas. These bubbles are deflected upwards by the baffle 167, and push their way past the ball 168, and out of the valve 164 through the sterile air barrier 173, as indicated by arrow B. The ball 168 preferably has a density less than that of the fluid in the tube 137 and the valve 164, and greater than the gas bubbles 175. Thus, when no gas bubbles are present in the fluid, the ball 168 is forced upwards against an area 176 of the valve body 171 which is of reduced diameter, and forms a seal when the ball 168 is pressed upwardly against it, thereby sealing any fluid from passing through the port 172. In addition, the sterile air barrier is preferably of a conventional hydrophobic material, such as polyvinylidene fluoride, which allows gas, but not liquids, to pass through. This not only inhibits fluid from passing through the port 172, but prevents contaminants from passing into the valve 164, thus maintaining system sterility.

When gas bubbles 175 are present in the fluid, the ball 168 tends to fall down from the seal 176, since it is denser than the gas. So long as gas is present in the fluid in the valve 164, the ball valve will be open, allowing the gas to escape through the port 172. As soon as the gas has all been purged, the ball 168 reseals against the seal 176, and the fluid 174, now purged of bubbles, flows out of the outlet 166, and through the tube 137 as indicated by arrow C in FIG. 10.

Modifications of the above described embodiment that are obvious to those of skill in the fields of mechanical engineering, infusion devices, and related technologies are intended to be within the scope of the following claims.

We claim:

1. A hand-held and operated pneumatically powered infusion/inflation device comprising in combination
   (a) a housing adapted to be gripped and held by a human hand and containing
   (b) a pressure vessel containing a gas under pressure
   (c) valve means connected to the vessel for alternatively venting the gas and directing it to an infusion chamber
   (d) an infusion chamber assembly comprising
      (i) a power chamber having an inlet for receiving said gas and being connected in tandem to
      (ii) an infusion chamber for holding an infusate having an outlet through which the infusate is ejected under the pressure exerted by said gas
      (iii) a two-headed piston contained within and spanning the power and infusion chambers with one head positioned in the drive chamber and receiving pressure from the gas and the other head positioned in the infusion chamber and placing pressure on the infusate (e) a second valve means connected to said outlet for controlling the pressurized flow of infusate from the infusion chamber; and (f) a conduit connected to said valve means for carrying the infusate from the valve to an infusion/inflation site.

2. The device of claim 1 including (g) a pressure regulator means interposed in the flow path of the gas between the pressure vessel and valve means for regulating the gas pressure to a predetermined level.

3. The device of claim 2 including (h) a safety relief valve means interposed in the flow path of the gas between the pressure vessel and valve means for preventing the gas pressure from exceeding the predetermined level.

4. The device of claim 2, wherein the pressure vessel is sealed and the device includes means for piercing the seal of the vessel to permit the gas to flow therefrom to said pressure regulator means.

5. The device of claim 4 wherein the means for piercing the seal of the vessel includes a fixed hollow needle and means for urging the vessel into contact with the needle so that the needle punctures the seal.

6. The device of claim 5 wherein the vessel is slidably received in a sleeve and the urging means is a hand-operated lever that carries a cam head that works against an end of the vessel to cause the vessel to slide within the sleeve and into contact with the needle.

7. The device of claim 6, further comprising means for preventing pressurized gas within said vessel from leaking to atmosphere.

8. The device of claim 7, wherein said leaking preventing means includes a resilient member disposed adjacent said vessel.

9. The device of claim 8, wherein said resilient member comprises an O-ring.

10. The device of claim 1 including biasing means for biasing the piston toward the inlet of the power chamber.

11. The device of claim 1, wherein said pressure vessel is sealed, said device further comprising means for unsealing said vessel for coupling said gas under pressure to said valve means.

12. The device of claim 11, wherein said unsealing means comprises a mechanism for piercing said vessel.

13. The device of claim 1, including a pressure gauge coupled to said infusion chamber for measuring a level of pressure of said infusate.

14. The device of claim 1, further comprising a flow control orifice disposed in said flow path for restricting flow of highly pressurized gas.

15. An apparatus for infusion of a fluid, comprising:
a first chamber for receiving a pressurized medium and having a first end and a second end;
a second chamber for receiving the fluid and having a third end and a fourth end;
a piston having a first head slidably mounted in said first chamber and a second head slidably mounted in said second chamber, where each of said heads seals against passage of the fluid and said pressurized medium;
first means for biasing said piston such that said first head is at said first end;
means coupled to said first end for providing said pressurized medium to said first chamber, for overcoming said first biasing means so as to force said first head towards said second end and to force said second head towards said fourth end;
a first valve coupled to said fourth end; and
means for communicating said fourth end and said first valve with a source of the fluid.

16. The apparatus of claim 15, wherein said means for providing said pressurized medium comprises:
a tube coupled to said first end for conveying said pressurized medium to said first chamber;
a second valve coupled to said tube and said first chamber for alternately: (a) providing a flow path for said pressurized medium between said tube and said first chamber, and (b) blocking said flow path and venting said first chamber.

17. The apparatus of claim 16, wherein said means for providing said pressurized medium further comprises a pressure relief mechanism, including a normally closed vent coupled to said tube for automatically opening when pressure within said tube exceeds a predetermined amount.

18. The apparatus of claim 17, wherein said pressure relief mechanism comprises a bore coupled to said tube, a third valve, and second means for biasing said third valve to a closed position for closing said bore, wherein said predetermined amount of pressure is determined by said second biasing means.

19. The apparatus of claim 15, further comprising means for biasing said first valve to a closed position when said first valve is not affirmatively forced open.

20. The apparatus of claim 15, further comprising a vent disposed between said first end and said fourth end, wherein said piston is configured such that said vent is in a region defined between said first end and said second end for all positions of said piston, for venting any of said pressurized medium which enters said region.

21. The apparatus of claim 15, further comprising a gas release valve mounted along said communicating means for purging said fluid of gas.

22. The apparatus of claim 21, wherein said gas release valve comprises:
an inlet;
a port coupled to said inlet and in communication with an exterior of said gas release valve;
a baffle for deflecting said gas and fluid towards said port;
an outlet coupled to said port and said inlet; and
means for passing said gas through said port while inhibiting passage of the fluid.

23. The device of claim 16, further comprising a flow control orifice disposed in said flow path for restricting flow of highly pressurized gas.

24. An apparatus for infusing a first fluid and a second fluid, comprising:
a first unit having a first interior for holding the first fluid and having a first output tube with a first proximal end and a first distal end, said first proximal end being connected to said first interior, with a first piston disposed within said first interior;
a second unit having a second interior for holding the second fluid and having a second output tube with a second proximal end and a second distal end, said second proximal end being connected to said second interior, with a second piston disposed within said second interior;
a first fluid supply tube coupled to said first output tube at a first connection point between said first proximal end and said first distal end, and connected to a first reservoir of said first fluid;

a first check valve disposed on said first fluid supply tube for preventing said first fluid from flowing from said first output tube into said first fluid supply tube;

a second fluid supply tube coupled to said second output tube at a second connection point between said second proximal end and said second distal end, and connected to a second reservoir of said second fluid;

a second check valve disposed on said second fluid supply tube for preventing said second fluid from flowing from said second output tube into said second fluid supply tube;

a third check valve positioned on said first output tube distally of said first connection point for blocking passage of any fluid in a direction from said first distal end towards said first proximal end; and a fourth check valve positioned on said second output tube distally of said second connection point for blocking passage of any fluid in a direction from said second distal end towards said second proximal end;

means coupled to said first and second units for moving said first and second pistons in a first direction so as to draw the first and second fluids from said first and second reservoirs through said first and second fluid supply tubes past said first and second check valves and thence through said first and second output tubes into said first and second interiors, respectively;

first and second means coupled to said first and second pistons, respectively, for driving said first and second pistons in a second direction for driving said first and second fluids from said first and second interiors, respectively, through said first and second output tubes past said third and fourth check valves and thence towards said first and second distal ends, respectively.

25. The apparatus of claim 24, further comprising:

a first input tube coupled to said first and second output tubes at said first and second distal ends by means of first and second connector tubes, respectively, for providing said first and second fluids to a first input location;

a second input tube coupled to said first and second output tubes at said first and second distal ends by means of third and fourth connector tubes, respectively, for providing said first and second fluids to a second input location; and a fluid control valve positioned on each of said first, second, third and fourth connector tubes for providing said first fluid, said second fluid, and both of said first and second fluids, alternatively, to said first and second input locations.

26. The apparatus of claim 25, further comprising a gas release valve mounted on each of said first and second output tubes for purging said first and second fluids of entrapped gas.

27. The apparatus of claim 26, wherein each said gas release valve comprises:

an inlet;

a port coupled to said inlet and in communication with an exterior of said gas release valve;

a baffle for deflecting said gas and fluid towards said port;

an outlet coupled to said port and said inlet; and means for passing said gas through said port while inhibiting passage of the fluid.

28. The apparatus of claim 24, wherein said means for moving said first and second pistons in said first direction comprises:

a source of pressurized fluid;

a first pressure line coupling said source to said first unit;

a second pressure line coupling said source to said second unit;

a first pressure line valve mounted on said first pressure line for controlling flow of said pressurized fluid to said first unit; and a second pressure line valve mounted on said second pressure line for controlling flow of said pressurized fluid to said second unit.

* * * * *